United States Patent [19]

Callander

[11] Patent Number: 5,681,962

[45] Date of Patent: Oct. 28, 1997

[54] PROCESS FOR PREPARING ARYL-PIPERIDINE CARBINOLS

[75] Inventor: Sidney Edward Callander, Worthing, England

[73] Assignee: SmithKline Beecham plc, Brentford, England

[21] Appl. No.: 522,403

[22] PCT Filed: Mar. 8, 1994

[86] PCT No.: PCT/EP94/00694

§ 371 Date: Sep. 6, 1995

§ 102(e) Date: Sep. 6, 1995

[87] PCT Pub. No.: WO94/21609

PCT Pub. Date: Sep. 29, 1994

[30] Foreign Application Priority Data

Mar. 13, 1993 [GB] United Kingdom .............. 9305175

[51] Int. Cl.[6] .................. C07D 211/22; C07D 211/40
[52] U.S. Cl. ................................ 546/219; 546/240
[58] Field of Search ............................ 546/219, 240

[56] References Cited

U.S. PATENT DOCUMENTS

| | | | |
|---|---|---|---|
| 4,007,196 | 2/1977 | Christensen et al. | 546/240 |
| 5,258,517 | 11/1993 | Zepp et al. | 546/240 |

FOREIGN PATENT DOCUMENTS

| | | |
|---|---|---|
| 0 223 334 | 5/1986 | European Pat. Off. |
| 0 374 675 | 6/1990 | European Pat. Off. |

OTHER PUBLICATIONS

Campaigne et al. "Reduction of 1-methyl-3methoxy-5-arylpyrrole carboxylic ester with selected reducing agents." J. Heterocycl. Chem. v. 12, pp. 317–319, 1975.

Chemical Abstracts, vol. 91, No. 25, 17 Dec. 79, Columbus, Ohio Abstract No. 211258g.

*Primary Examiner*—Ceila Chang
*Attorney, Agent, or Firm*—Edward T. Lentz; Stephen Venetianer; Charles M. Kinzig

[57] ABSTRACT

A process for the preparation of a compound of formula (I)

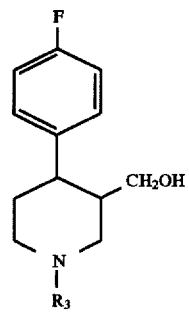

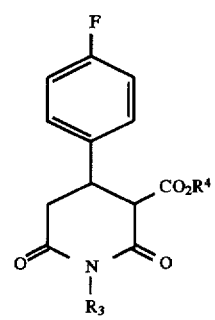

in which $R_3$ is hydrogen, $C_{1-6}$ alkyl or $C_{1-6}$ alkylaryl, by reduction using diborane, of a compound of Formula (II) in which $R_3$ is as defined in relation to formula (I) and $R^4$ is $C_{1-6}$ alkyl.

8 Claims, No Drawings

PROCESS FOR PREPARING ARYL-PIPERIDINE CARBINOLS

This application is a 371 of PCT/EP94/00194 filed Mar. 8, 1994.

The present invention relates to a novel process for preparing aryl-piperidine carbinols.

U.S. Pat. No. 4,007,196 describes certain compounds which are described as possessing anti-depressant activity.

An intermediate in the preparation of the above mentioned compounds is a compound of formula (A):

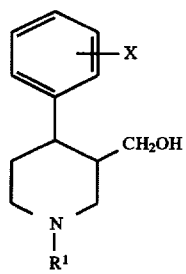

wherein R¹ represents hydrogen, trifluoro ($C_{1-4}$) alkyl, alkyl or alkynyl, and X represents hydrogen, alkyl having 1–4 carbon atoms, alkoxy, trifluoroalkyl, hydroxy, halogen, methylthio, or aralkyloxy.

The compounds of formula (A) are disclosed as having pharmacological properties that make them useful as anti-depressants.

One particular compound of formula (A) has been found to be especially effective as an anti-depressant. This compound is known as paroxetine and has the following formula:

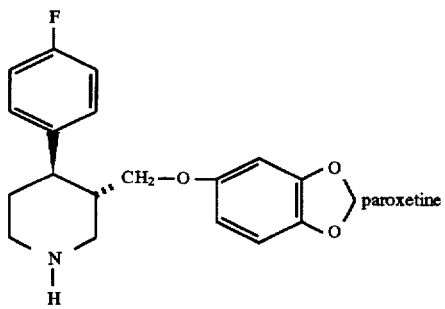

U.S. Pat. No. 4,902,801 describes the preparation of compounds of formula (B):

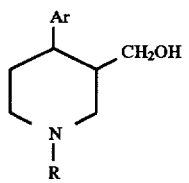

wherein Ar represents an aryl or substituted aryl group and R represents hydrogen, an alkyl or aralkyl group; by reduction of a compound of formula (C):

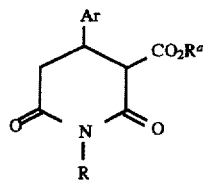

wherein Ar and R are as defined for formula (B), and $R^a$ is an alkyl group.

Such a process is described as being suitable for preparing the precursor compounds of formula (B) to paroxetine.

The only specially disclosed reducing agents for carrying out the process described in U.S. Pat. No. 4,902,801 are lithium aluminium hydride or aluminium hydride. These reducing agents are expensive, difficult to handle and are associated with a large exotherm which creates process control problems when carrying out the reaction on a large scale.

The present invention surprisingly overcomes or alleviates the above problems by the use of diborane as the reducing agent. It also gives a better yield and is more economical.

Accordingly, the present invention provides a process for the preparation of compound of formula (I):

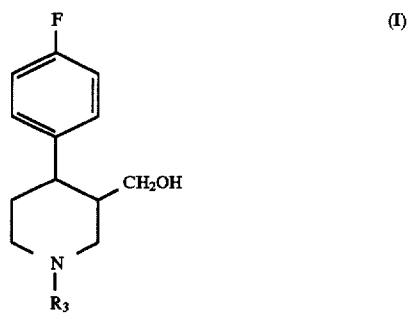

in which $R_3$ is hydrogen, $C_{1-6}$ alkyl or $C_{1-6}$ alkylaryl, by reduction using diborane, of a compound of formula (II):

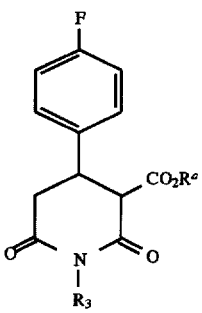

in which $R_3$ is as defined in relation to formula (I) and $R_4$ is $C_{1-6}$ alkyl.

Preferably $R_3$ is methyl.

Preferably $R_4$ is ethyl or methyl or a mixture of ethyl/methyl.

The reaction is suitably carried out in an inert solvent such as tetrahydrofuran or dimethoxyethane (DME).

The diborane is suitably generated in situ by the addition of boron trifluoride etherate to sodium borohydride in the presence of the compound of formula (II), at reduced temperature such as −10° to 20° C., preferably at 0° to 5° C. Alternatively, and more preferably for safety and handling reasons diborane is generated by the addition of hydrogen chloride gas (which can suitably be dissolved in an inert solvent such as DME) to sodium borohydride in the presence of the compound of formula (II), at reduced temperature such as −10° C. to 20° C., preferably at 0° to 5° C.

Once the addition of the boron trifluoride etherate or the hydrogen chloride gas is complete, the reaction is suitably allowed to warm to ambient or elevated temperature for example 20° to 60° C. more preferably 20° to 40° C.

The reaction may then be terminated or "quenched" by the addition of the reaction mixture to a mineral acid such as aqueous hydrochloric acid or by the addition of a mineral acid such as aqueous hydrochloric acid to the reaction mixture. Any resulting solid may then be filtered off and the product compound of formula (I) may be isolated by distilling off the reaction solvent, replacing it with a suitable solvent from which the product may be precipitated from, such as toluene, and precipitating the product by the addition of a suitable precipitating solvent such as n-heptane suitably after concentration of the solution of the product.

The present invention also provides a process for the preparation of paroxetine or a pharmaceutically acceptable salt thereof, especially the hydrochloride hemi-hydrate, which comprises forming a compound of formula (I) as described above and thereafter subsequently converting it to paroxetine or a pharmaceutically acceptable salt thereof using conventional techniques especially those described in U.S. Pat. Nos. 4,902,801 and 4,721,723.

The following examples illustrate the present invention.

EXAMPLE 1

(±)-trans-4-(4'-fluorophenyl)-3-hydroxymethyl-N-methyl-piperidine

Input *

(±) trans-3-Ethoxy/methoxycarbonyl-4-(4'-fluorophenyl)-N-methyl piperidine-2,6-dione 15.3 g assay 93.7%

Sodium Borohydride 6.3 g

Boron Trifluoride etherate 18 ml

Tetrahydrofuran (THF) 75 ml

Toluene 200 ml

3N HCL 40 ml

Heptane 70 ml

40% sodium hydroxide solution 25 ml

Method—The following methodology was carried out

1) To 50 ml THF add 6.3 g sodium borohydride
2) Cool solution to 0°–5° C.
3) Dissolve 15.3 g (±) trans-3-Ethoxy/methoxycarbonyl-4-(4'-fluorophenyl)-N-methyl piperidine-2,6-dione 1 in 25 ml THF. Add over ca 5 minutes to borohydride solution keeping temperature at 0°–5° C.
4) Add slowly to solution 18 ml etherate over ca 15 minutes keeping temperature at 0° to 5° C.
5) Allow temperature to rise to 20° C. over ca 1 hour
6) Warm solution to 35°–40° C. for 2 hours
7) Cool solution to 0°–5° C.
8) Inversely add solution slowly to 40 ml 3N HCL allowing temperature to rise to 20°–25° C.
9) Cool solution to 5° C. and filter off boric acid solid
10) Wash filter with 20 ml water.
11) Reflux solution at 65° C. to collect THF
12) Allow temperature of solution to rise to 100° C.
13) Add 50 ml water\75 ml toluene to cool solution to 60° C.
14) Separate lower aqueous layer
15) Add further 50 ml water to toluene keeping the temperature at 60° C.
16) Separate and collect aqueous fractions
17) Add 75 ml toluene to the aqueous fraction. Take pH to 12–12.5 and separate the layers.
18) Add further 50 ml toluene to aqueous and separate
19) Combine toluene phases and evaporate to ca 20 g
20) Add 50 ml heptane, cool to 5° C. and filter
21) Wash filter with 20 ml heptane
22) Dry in vac oven overnight 40° C.
Wt isolated 9.6 g
Assay 97%
Yield 85%.

Assays were performed using high performance liquid chromatography.

Prepared according to the procedures outlined in U.S. Pat. No. 4,902,801.

EXAMPLE 2

Synthesis of (±)-trans-4-(4'-fluorophenyl)-3-hydroxymethyl-N-methyl piperidine *

Input (+,−)- trans-3-Ethoxy/methoxycarbonyl-4-(4'-fluorophenyl)-N-methyl-piperidine—15.3 g as is Sodium Borohydride—8.0 g Hydrogen chloride gas—6.5 g Dimethoxyethane (DME)—150 ml Toluene—50 ml 3N Hydrochloric acid solution—60 ml Heptane—20 ml 40% sodium hydroxide solution—25 ml Method—The following methodology was carried out 1. Add sodium borohydride (8.0 g) to DME (75 ml).
2. Cool the solution to 0°–5° C.
3. Dissolve (+,−)-trans-3-ethoxy/methoxycarbonyl-4-(4'-fluorophenyl)N-methyl piperidine (15.3 g) in DME (25 ml) and add to the sodium borohydride slurry maintaining the temperature at 0°–5° C.
4. Dissolve hydrogen chloride gas (6.5 g) in DME (50 ml).
5. Add the hydrogen chloride/DME solution to the borohydride slurry maintaining the temperature at 0°–5° C. During this period the reaction is nitrogen blanketed and hydrogen is liberated.
6. Stir the reaction mixture at 0°–5° C. for 30 mins.
7. Warm the mixture to 35°–40° C. and stir for 2 hours.
8. Cool the reaction mixture to 0°–5° C.
9. Quench the reaction by adding 3N hydrochloric acid solution (60 ml) maintaining the temperature below 20° C.
10. Charge water (50 ml) to the reaction mixture maintaining the temperature below 20° C.
11. Distil the solution up to 95° C. and collect the wet DME solution (ca. 150 ml).

12. Add toluene (50 ml) and allow the temperature to fall to 80° C.
13. Separate the phases.
14. Cool the aqueous phase to 50°–55° C. and charge heptane (20 ml).
15. Charge sodium hydroxide solution to pH the solution to 11.0–11.5 whilst maintaining the temperature at 50°–55° C.
16. Cool the mixture to 5°–10° C. over at least 30 mins.
17. Filter off the product.
18. Wash the product with water (2×20 ml).
19. Dry the product at ca. 40° C.
   Typical isolated weight—9.1 g
   Typical purity 90–95%
   Typical yield 78–80%

Prepared according to the procedures outlined in U.S. Pat. No. 4,902,801.

I claim:

1. A process for the preparation for compound of formula (I):

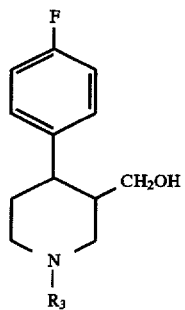

in which $R_3$ is hydrogen, $C_{1-6}$ alkyl or $C_{1-6}$ alkylaryl, by reduction using diborane generated in situ, at −10° C. to 20° C., in an inert solvent, of a compound of formula (II):

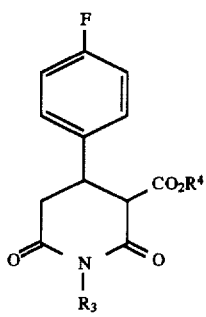

in which $R_3$ defined in relation to formula (I) and $R_4$ is $C_{1-6}$ alkyl.

2. A process according to claim 1 in which $R_3$ is methyl.

3. A process according to claim 2 in which $R_4$ is ethyl or methyl.

4. A process according to claim 3 in which the reaction is carried out in tetrahydrofuran or dimethoxyethane.

5. A process according to claim 4 in which the diborane is generated by the addition of boron trifluoride etherate to sodium borohydride in the presence of a compound of formula (II).

6. A process according to claim 5 in which the diborane is generated by the addition of hydrogen chloride gas to sodium borohydride in the presence of a compound of formula (II).

7. A process according to claim 1 and thereafter converting the resulting compound of formula (I) to paroxetine or a pharmaceutically acceptable salt thereof.

8. A process according to claim 7 in which the pharmaceutically acceptable salt thereof is the hydrochloride hemihydrate.

* * * * *